(12) United States Patent
Jablonski

(10) Patent No.: US 9,333,314 B2
(45) Date of Patent: May 10, 2016

(54) PATIENT INTERFACE WITH TORQUE-RESISTANT CONNECTION

(71) Applicant: Gregory John Jablonski, Butler, PA (US)

(72) Inventor: Gregory John Jablonski, Butler, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 495 days.

(21) Appl. No.: 13/621,373

(22) Filed: Sep. 17, 2012

(65) Prior Publication Data

US 2013/0068230 A1    Mar. 21, 2013

Related U.S. Application Data

(60) Provisional application No. 61/536,700, filed on Sep. 20, 2011.

(51) Int. Cl.
*A61M 16/06* (2006.01)
*A61M 16/08* (2006.01)

(52) U.S. Cl.
CPC ........... *A61M 16/06* (2013.01); *A61M 16/0683* (2013.01); *A61M 16/0816* (2013.01); *A61M 2205/0216* (2013.01)

(58) Field of Classification Search
CPC .............. A61M 16/06–16/1694; A62B 18/02; A62B 18/025; A62B 18/06; A62B 18/086
USPC .......................... 128/205.25, 206.21–207.13
See application file for complete search history.

(56) References Cited

U.S. PATENT DOCUMENTS

| | | | | |
|---|---|---|---|---|
| 4,470,413 A | * | 9/1984 | Warncke | 128/201.18 |
| 6,039,044 A | * | 3/2000 | Sullivan | 128/205.25 |
| 6,192,886 B1 | * | 2/2001 | Rudolph | 128/207.13 |
| 7,647,928 B2 | * | 1/2010 | Muellinger et al. | 128/206.22 |
| 7,861,715 B2 | | 1/2011 | Jones | |
| 2007/0125384 A1 | * | 6/2007 | Zollinger et al. | 128/206.24 |
| 2008/0006276 A1 | * | 1/2008 | Kreutzmann et al. | 128/206.24 |
| 2009/0084385 A1 | * | 4/2009 | Lang | 128/206.21 |
| 2010/0018534 A1 | | 1/2010 | Veliss | |
| 2010/0282264 A1 | * | 11/2010 | Chang | 128/206.21 |
| 2013/0133664 A1 | * | 5/2013 | Startare et al. | 128/206.24 |

FOREIGN PATENT DOCUMENTS

EP    1258266 A1    11/2002

* cited by examiner

*Primary Examiner* — Valerie L Skorupa
(74) *Attorney, Agent, or Firm* — Michael W. Haas

(57) ABSTRACT

An patient interface that reliably maintains a seal between it and the patient. The patient interface advantageously includes a deformation portion at its point of connection with an air supply, with the deformation portion being relatively more deformable than the other portions of the patient interface in order to resist torque applied by the air supply from disturbing the seal between the patient interface and the patient. While the air supply is pivotably connected with the patient interface and is pivotable about a pivot axis, a torque applied about an axis other than the pivot axis results in deformation of the deformation portion and thus advantageously avoids breaking the seal between the patient interface and the patient.

12 Claims, 6 Drawing Sheets

PATIENT INTERFACE WITH TORQUE-RESISTANT CONNECTION

CROSS-REFERENCE TO RELATED APPLICATIONS

This patent application claims the priority benefit under 35 U.S.C. §119(e) of U.S. Provisional Application No. 61/536,700 filed on Sep. 20, 2011, the contents of which are herein incorporated by reference.

BACKGROUND OF THE INVENTION

1. Field of the Invention

The present invention pertains to respiratory interface devices and, in particular, to an improved mask that is retained with improved reliability on a patient.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder such as sleep apnea syndrome in particular, obstructive sleep apnea (OSA), or congestive heart failure.

Non-invasive ventilation and pressure support therapies involve the placement of a respiratory patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or full face mask that covers the patient's face. The respiratory patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head. Because such respiratory patient interface devices are typically worn for an extended period of time, it is important for the headgear to maintain the mask component of the device in a tight enough seal against the patient's face without discomfort.

For respiratory patient interface devices, a key engineering challenge is to balance patient comfort against stability of the device. As a patient changes sleeping positions through the course of the night, the mask portions of respiratory patient interface devices may become dislodged, and the seal against the patient may be broken. A dislodged mask portion can be stabilized by the increasing strapping force provided by the headgear, but increased strapping force tends to reduce patient comfort. This design conflict is further complicated by the widely varying facial geometries that a given respiratory patient interface device design needs to accommodate.

SUMMARY OF THE INVENTION

Accordingly, it is an object of the present invention to provide an improved patient interface that more reliably maintains a seal between it and the patient. The patient interface advantageously includes a deformation portion at its point of connection with an air supply, with the deformation portion being relatively more deformable than the other portions of the patient interface in order to resist torque applied by the air supply from disturbing the seal between the patient interface and the patient. While the air supply is pivotably connected with the patient interface and is pivotable about a pivot axis, a torque applied about an axis other than the pivot axis results in deformation of the deformation portion and thus advantageously avoids breaking the seal between the patient interface and the patient.

Another object of the present invention to provide an improved patient interface that is resistant to certain torques applied thereto by an air supply line.

Another object of the present invention is to provide an improved patient interface having a deformation portion that is configured to deform in response to a torque applied by an air supply line in order to maintain the integrity of the seal between patient interface and the patient.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENT

Figure 1:
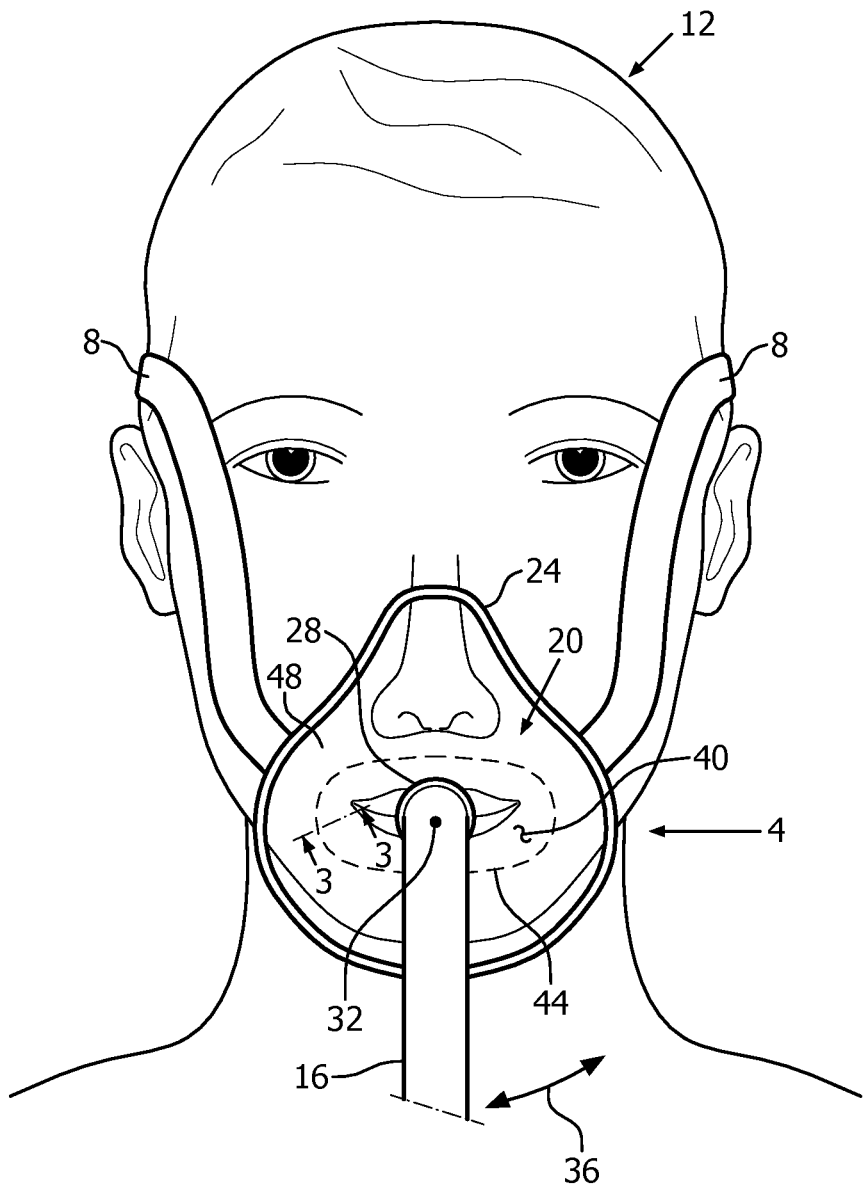
FIG. 1 is a front elevational view of an improved patient interface in accordance with a first embodiment of the invention disposed on a patient and being in a free state.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

An improved patient interface 4 in accordance with the present invention is depicted in FIG. 1 as being connected to a headgear 8 and mounted on a patient 12. As is understood in the relevant art, patient interface 4 is configured to provide a therapeutic flow of breathing gases to patient 12.

More particularly, patient interface 4 is in fluid communication with the mouth and nose of patient 12 in order to provide the flow of breathing gases to patient 12. Patient interface 4 is connectable with an air supply line 16, also referred to herein merely as a "supply", that provides the flow of breathing gases. As is understood in the relevant art, the flow of breathing gases may be any gas or combination of gases and, more particularly, may be air. Supply line 16 is also known as a "patient circuit" and can include features and accessories typically found on such tubing, such as exhaust ports, filters, humidification elements, sensors, etc. Supply line 16 is typically a flexible conduit having one end connected to a pressure generating device (not shown) and the other end connected to patient interface 4. An elbow connector may be used to connect the supply line to the mask body or shell.

Figure 2:
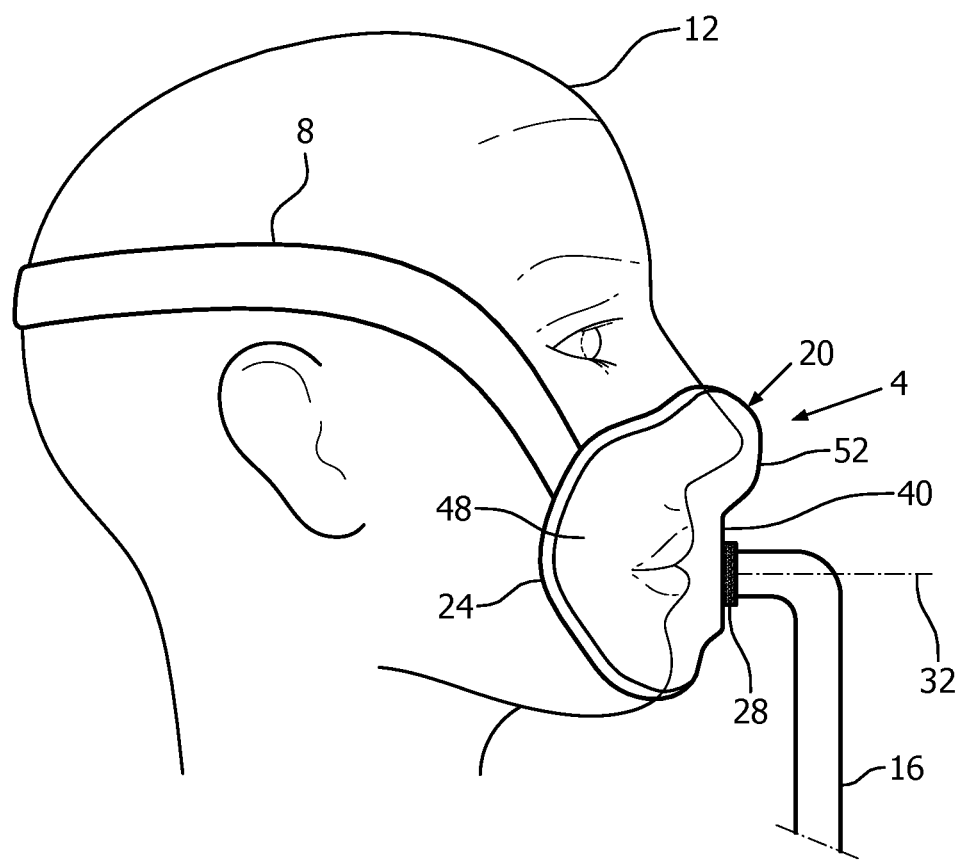
FIG. 2 is a side elevational view of the improved patient interface of FIG. 1.

As can be understood from FIGS. 1 and 2, patient interface 4 includes a mask body 20 (also known as a mask shell) and a flange apparatus 24 that are connected together. The flange apparatus is typically a cushion or other sealing element that provides a sealed interface with the surface of the patient. Patient interface 4 may be configured in any of a variety of fashions, but most likely is formed in a unitary fashion out of a resilient, translucent silicone material, although other materials can be employed without limitation.

When mask body 20 is installed on patient 12, as is indicated in FIGS. 1 and 2, a chamber is formed between the face of patient 12 and what becomes the internal (opposed) surface of mask body 20. The chamber is in fluid communication with both supply 16 and with the airways of patient 12. Flange apparatus 12 engages the skin of the face of patient 12 and forms a seal therebetween that is essentially airtight within the range of the air pressures that are typically experienced in providing therapeutic air or other breathing gases to patient 12.

Figure 4:
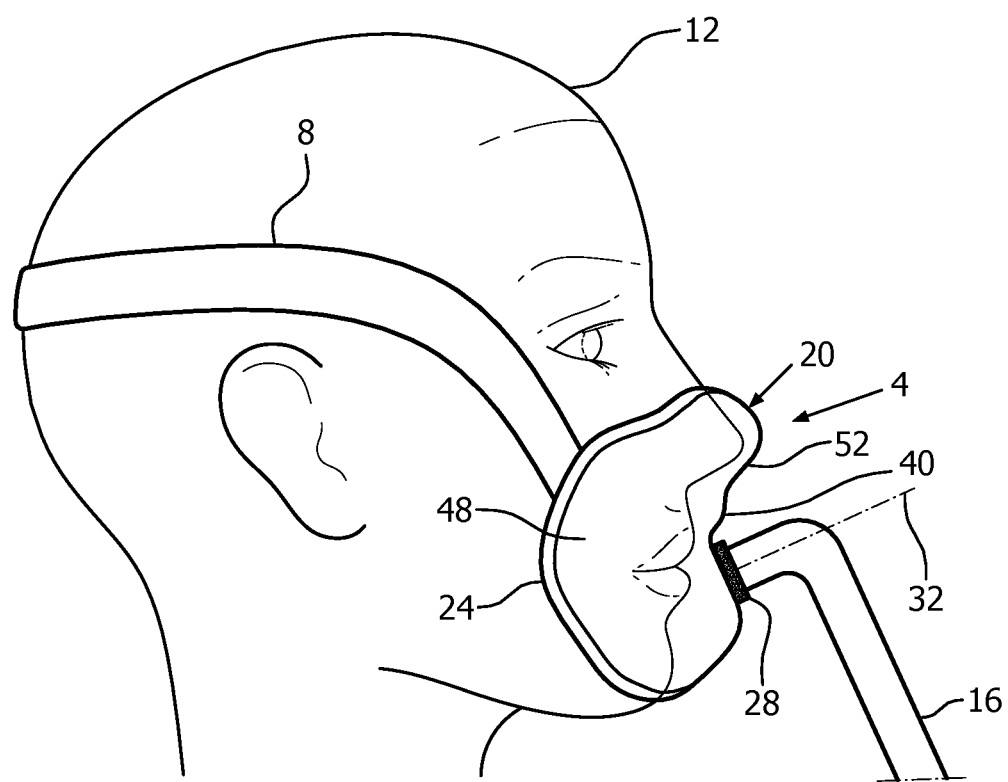
FIG. 4 is view similar to FIG. 2, except depicting the patient interface having an upward torque applied thereto by a connected air supply line.
Figure 5:
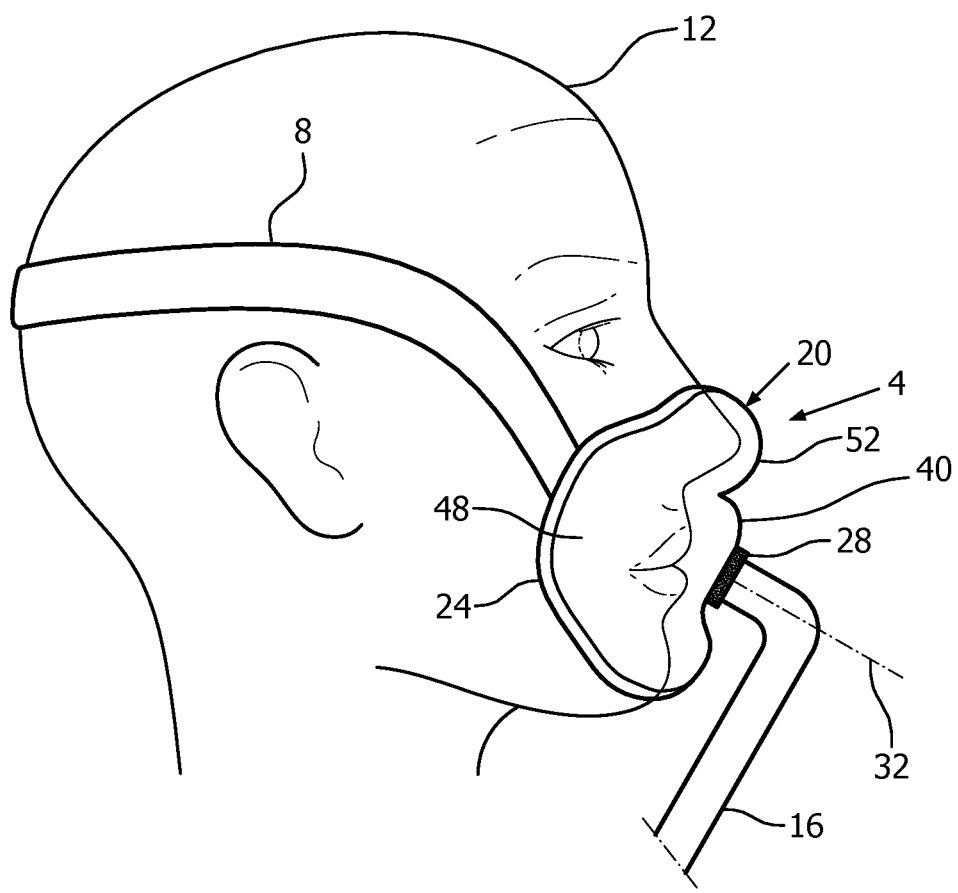
FIG. 5 is view similar to FIG. 4, except having an upward torque applied to the patient interface.

Mask body 20 includes a connection 28 at which location supply 16 is connected with patient interface 4. Typically this connection is a pivotable connection to that the supply line can rotate relative to mask body 20. Supply 16 is pivotable with respect to patient interface 4, and, more particularly, is pivotable with respect to mask body 20. Such pivoting of supply 16 with respect to mask body 20 is in the form of pivoting motion about a pivot axis 32, which is shown in FIGS. 2 and 4-5, and which extends into the plane of the page of FIG. 1. Pivoting motion of supply 16 with respect to mask body 20 is depicted with a motion arrow 36 in FIG. 1. Flange apparatus 24 is situated peripheral to mask body 20 and, in the depicted exemplary embodiment, extends about the entire periphery of mask body 20.

Mask body 20 includes a deformation portion 40 that is situated at an anterior end of mask body 20 and which, in the depicted exemplary embodiment, is situated peripheral to connection 28. In the exemplary embodiment, deformation portion 40 extends about the entire periphery of connection 28, i.e., deformation portion 40 extends about the entire circumference of connection 28. It is noted, however, that in other embodiments not expressly depicted herein, the deformation portion potentially could extend about less than the entire periphery of connection 28 without departing from the present concept so long as the resultant deformation portion is sufficiently deformable to maintain the integrity of the airtight seal between flange apparatus 24 and patient 12.

Figure 6:
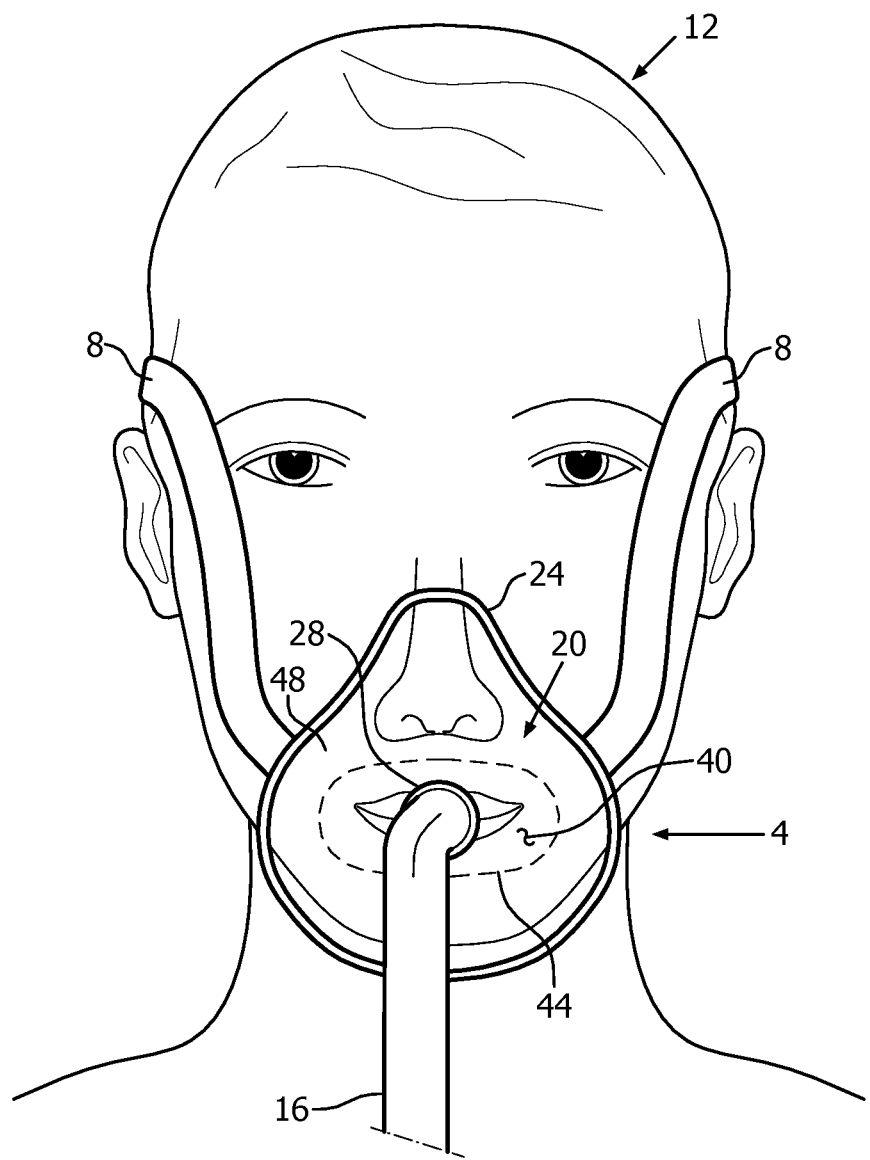
FIG. 6 is view similar to FIG. 1, except depicting the patient interface having a leftward torque applied thereto by the air supply line.

Deformation portion 40 can be said to extend generally between connection 28 and a line that is indicated at the numeral 44 in FIGS. 1 and 6. As can be understood from FIG. 1 and, more particularly, from line 44, deformation portion 40 is generally elliptical in shape having its major axis extending horizontally from the perspective of FIG. 1 and having its minor axis extending vertically from the perspective of FIG. 1. The major axis, i.e., the width of deformation portion 40 in a direction parallel with a transverse plane of patient 12, is greater than the minor axis, i.e., the height of deformation portion 40 in a direction parallel with a sagittal plane of patient 12.

Mask body 20 can also be said to include a support portion 48 that is situated peripheral to deformation portion 40 and most of which extends in a direction posterior to deformation portion 40. It is understood that terms such as "anterior", "posterior", "transverse plane", "sagittal plane", and the like, and variations thereof, are intended to refer to directions or references from the perspective of patient interface 4 being mounted on patient 12, as is indicated in the figures herein.

As can be seen in FIG. 2, in an exemplary embodiment, support portion 48 includes a superior protrusion 52 that extends in an anterior direction in the vicinity of the nose of patient 12. Moreover, it can be seen from FIG. 1 that deformation portion 40 is situated generally inferior to the nose of patient 12. It can therefore be understood FIGS. 1 and 2 that deformation portion 40 is situated generally inferior to superior protrusion 52. Please note that superior protrusion 52 shown at the nose is optional. The present invention contemplates that superior protrusion 52 can be eliminated or modified to have other structures, sizes and/or configurations.

Figure 3:
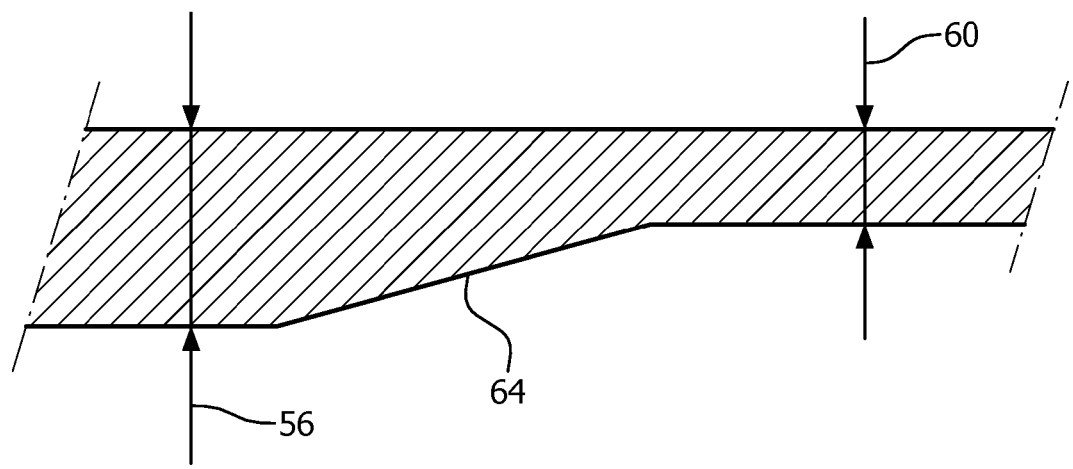
FIG. 3 is sectional view as taken along line 3-3 of FIG. 1.

Support portion 52 is of a support nominal thickness 56 which may be in the range of about 0.080-0.090 inches, as is depicted in FIG. 3. Deformation portion 40 is of a deformation nominal thickness 60 which is in the range of about 0.040-0.050 inches, as is likewise depicted in FIG. 3. It can be seen therefore, that in response to any loading from supply 16 other than a torque about pivot axis 32, deformation portion 40 will deform to a much greater extent than any portion of support portion 48. Because such loading would be at connection 28, which is situated generally centrally on deformation portion 40 in the depicted exemplary embodiment, the portions of mask body 20 that are nearest to connection 28 will experience the greatest degree of loading and thus would ordinary deform to a greater extent in a response to a given load than portions of mask body 20 that are spaced farther away from such loading.

However, by additionally configuring deformation portion 40 to have deformation nominal thickness 60 which is on the order of only about one half the thickness of support nominal thickness 56, it can be understood that deformation portion 40 will experience nearly all of the meaningful deformation of mask body 20 that occurs in response to loading other than a rotation about pivot axis 32. Advantageously, therefore, the seal between flange apparatus 24 and patient 12 is maintained, thus enabling the therapeutic flow of breathing air supplied by supply 16 to be received by patient 12. That is, by absorbing the loading through deformation of deformation portion 40 rather than through deformation of support portion 48, torques and other loads that are other than about pivot axis 32 are effectively absorbed by deformation portion 40 without affecting the seal between mask body 20 and patient 12.

It can be seen that deformation portion 40 includes a transition region 64 that extends along line 44 at the transition between deformation portion 40 and support portion 48. While transition region 64 could merely be a step between deformation nominal thickness 60 and support nominal 56, a ramped transition such as is indicated at the numeral 64 in FIG. 3 has the added advantage of distributing stresses such as tensile and other stresses along transition region 64 rather than concentrating such stresses at a more limited location.

The exemplary support nominal thickness 56 has been indicated above as being in the range of about 0.080-0.090 inches, and the exemplary deformation nominal thickness 60 has been indicated above as being in the range of about 0.040-0.050 inches. It is noted however, that other thicknesses and relationships between the thicknesses can be employed without departing from the present concept. For instance, deformation nominal thickness 60 may be more broadly characterized as being in the range of about forty percent to sixty percent of support nominal thickness 56, although this range is intended to be exemplary only and not limiting.

FIGS. 4 and 5 depict the deformation of deformation portion 40 in response to an upward torque loading and a downward torque loading, respectively, by supply 16 on mask body 20. As can be understood from FIGS. 4 and 5, deformation portion 40 deforms in response to such loading, but support portion 48 experiences little, if any deformation. This advantageously maintains the integrity of the airtight seal between patient interface 4 and patient 12. Similarly, FIG. 6 depicts a lateral torque resulting from movement of supply 16 in the leftward direction from the perspective of FIG. 6. Again, such torque results in deformation that is experienced by deformation portion 40 without support portion 48 experiencing any meaningful deformation. Stated otherwise, support portion 48 experiences no deformation that would be of sufficient magnitude to disturb the airtight seal between patient interface 4 and patient 12.

It is noted that support portion 48 is depicted herein as being of a thickness represented by support nominal thickness 56 that is substantially constant throughout the extent of support portion 48. It is noted that deformation portion 40 is depicted herein as having a generally fixed cross-sectional thickness represented by deformation nominal thickness 60. It can be understood, however, that deformation portion 40 can be of other thicknesses in various regions without departing from the present concept. For instance, it may be determined that a particular patient experiences more loading in one direction than in another during sleeping hours, and it may be desirable therefore to provide an even thinner wall thickness in the vicinity of the resultant deformation in order to further ensure that the seal between patient interface 4 and patient 12 is not disturbed. Alternatively or additionally, deformation portion 40 may be of a transitional cross-sectional thickness rather than of a nominal thickness. For instance, this may mean that transition region 64 may occupy a larger portion of deformation portion 40 or may constitute the entirety of deformation portion 40. Such a ramped increase in thickness of deformation portion 40 in a direction away from connection 28 would have the effect of even further concentration the deformation of deformation portion 40 in the immediate vicinity of connection 28. Further variations will be apparent to those of ordinary skill in the art.

Patient interface 4 thus advantageously permits pivoting of supply 16 about pivot axis 32 with respect to patient interface 4, which is desirable, and which does not result in any deformation loading of patient interface 4. However, patient interface 4 responds to any other type of loading between supply 16 and patient interface 4 by having deformation portion 40 deform without any meaningful deformation of support portion 48. Advantageously, therefore, virtually any loading from supply 16 on patient interface 4 does not affect the airtight seal between patient interface 4 and patient 12, which promotes the provision of a therapeutic flow of breathing air to patient 12.

In certain embodiments, the general nature of the invention can be stated as including a patient interface structured to provide a flow of breathing gases to a patient, with the patient interface being further structured to be connected with a headgear for mounting the patient interface to the patient and to be connected with a supply that is structured to supply the flow of breathing gases to the patient interface. The patient interface can be generally stated as including a mask body, and as further including a flange apparatus connected peripherally with the mask body and being structured to engage the patient. The mask body can be generally stated as including a connection structured to be connected with the supply, a deformation portion situated peripheral to the connection, and a support portion connected with and extending in a direction generally posterior from the deformation portion and being connected with the flange apparatus. The support portion is of a nominal thickness. At least a part of the deformation portion is of another nominal thickness less than the nominal thickness and is structured to be relatively more deformable than the support portion in response to a torque input at the connection.

In certain embodiments, the general nature of the invention can be stated as including a patient interface structured to provide a flow of breathing gases to a patient, with the patient interface being further structured to be connected with a headgear for mounting the patient interface to the patient and to be connected with a supply that is structured to supply the flow of breathing gases to the patient interface. The patient interface can be generally stated as including a mask body, and as further including a flange apparatus connected peripherally with the mask body and being structured to engage the patient. The mask body can be stated as including a connection structured to be connected with the supply and to permit pivotable movement between the supply and the mask body about a pivot axis that extends generally centrally through the connection.

The mask body can be further stated as including a deformation portion situated peripheral to the connection, and a support portion connected with and extending in a direction generally posterior from the deformation portion and being connected with the flange apparatus. At least a part of the deformation portion is structured to be relatively more deformable than the support portion in response to a torque input at the connection about an axis other than the pivot axis.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface structured to provide a flow of breathing gases to a patient, the patient interface being further structured to be connected with a headgear for mounting the patient interface to the patient and to be connected with a supply (16) that is structured to supply the flow of breathing gases to the patient interface, the patient interface comprising:
    a mask body;
    a flange apparatus connected to the mask body and being structured to engage the patient, wherein the mask body comprises:
        a connection structured to be connected with the supply,
        a deformation portion situated peripheral to the connection, and
        a support portion connected with and extending in a direction generally posterior from the deformation portion and being connected with the flange apparatus; the support portion being of a nominal thickness, and wherein a part of the deformation portion has another nominal thickness less than the nominal thickness and structured to be relatively more deformable than the support portion in response to a torque input at the connection;
    wherein the another nominal thickness remains substantially constant throughout the part of the deformation portion; and
    wherein a transition part of the deformation portion extends from the part of the deformation portion having the substantially constant another nominal thickness and is of a thickness that transitions in a ramped fashion between the nominal thickness and the another nominal thickness to thereby distribute stresses from the torque input along the transition part rather than concentrating such stresses at a more limited location.

2. The patient interface of claim 1, wherein the deformation portion extends about substantially the entirety of the periphery of the connection.

3. The patient interface of claim 1, wherein the another nominal thickness is in the range of about forty percent to sixty percent of the nominal thickness.

4. The patient interface of claim 1, wherein the nominal thickness remains substantially constant throughout the extent of the support portion.

5. The patient interface of claim 1, wherein the width of the deformation portion in a direction parallel with the transverse plane of the patient is greater than the height of the deformation portion in a direction parallel with the sagittal plane of the patient.

6. The patient interface of claim 5, wherein the deformation portion is of a roughly elliptical shape of which the width and the height are the major and minor axes, respectively.

7. A patient interface structured to provide a flow of breathing gases to a patient, the patient interface being further structured to be connected with a headgear for mounting the patient interface to the patient and to be connected with a supply that is structured to supply the flow of breathing gases to the patient interface, the patient interface comprising:
    a mask body; and
    a flange apparatus connected peripherally with the mask body and being structured to engage the patient;
    the mask body comprising:
        a connection structured to be connected with the supply and to permit pivotable movement between the supply and the mask body about a pivot axis that extends generally centrally through the connection,
        a deformation portion situated peripheral to the connection,
        a support portion connected with and extending in a direction generally posterior from the deformation portion and being connected with the flange apparatus, and
        a part of the deformation portion being structured to be relatively more deformable than the support portion in response to a torque input at the connection about an axis other than the pivot axis;
    the support portion being of a nominal thickness;
    the part of the deformation portion being of another nominal thickness that remains substantially constant throughout the part of the deformation portion and that is less than the nominal thickness; and
    a transition part of the deformation portion extending from the part of the deformation portion having the substantially constant another nominal thickness and being of a thickness that transitions in a ramped fashion between the nominal thickness and the another nominal thickness to thereby distribute stresses from the torque input along the transition part rather than concentrating such stresses at a more limited location.

8. The patient interface of claim 7, wherein the deformation portion extends about substantially the entirety of the periphery of the connection.

9. The patient interface of claim 7, wherein the another nominal thickness is in the range of about forty percent to sixty percent of the nominal thickness.

10. The patient interface of claim 7, wherein the nominal thickness remains substantially constant throughout the extent of the support portion.

11. The patient interface of claim 7, wherein the width of the deformation portion in a direction parallel with the transverse plane of the patient is greater than the height of the deformation portion in a direction parallel with the sagittal plane of the patient.

12. The patient interface of claim 11, wherein the deformation portion is of a roughly elliptical shape of which the width and the height are the major and minor axes, respectively.

* * * * *